United States Patent [19]
Alsmeyer et al.

[11] Patent Number: 5,610,836
[45] Date of Patent: Mar. 11, 1997

[54] PROCESS TO USE MULTIVARIATE SIGNAL RESPONSES TO ANALYZE A SAMPLE

[75] Inventors: Daniel C. Alsmeyer; Vincent A. Nicely, both of Kingsport, Tenn.

[73] Assignee: Eastman Chemical Company, Kingsport, Tenn.

[21] Appl. No.: 594,217

[22] Filed: Jan. 31, 1996

[51] Int. Cl.$^6$ .................................................. G01N 33/00
[52] U.S. Cl. ..................... 364/498; 73/1 R; 364/571.04
[58] Field of Search ................. 73/1 R, 1 G; 364/498, 364/571.01–571.08, 582

[56] References Cited

U.S. PATENT DOCUMENTS

| | | | |
|---|---|---|---|
| 4,660,151 | 4/1987 | Chipman et al. | 364/498 |
| 4,661,913 | 4/1987 | Wu et al. | 364/500 |
| 5,121,337 | 6/1992 | Brown | 364/498 |
| 5,170,367 | 12/1992 | Mackay et al. | 364/571.01 |
| 5,243,546 | 9/1993 | Maggard | 364/571.02 |
| 5,440,388 | 8/1995 | Erickson | 356/346 |
| 5,446,681 | 8/1995 | Gethner et al. | 364/571.04 X |
| 5,455,177 | 10/1995 | Krause et al. | 73/1 R X |
| 5,455,673 | 10/1995 | Alsmeyer et al. | 356/301 |
| 5,459,677 | 10/1995 | Kowalski et al. | 73/1 R X |
| 5,475,220 | 12/1995 | Hughes et al. | 250/339.09 |
| 5,498,875 | 3/1996 | Obremski et al. | 250/458.1 |

OTHER PUBLICATIONS

Stark et al., "Near–Infrared Analysis (NIRA): A Technology for Quantitative and Qualitative Analysis," *Appl. Spec. Rev.* 1986, 22, pp. 335–399.

Miller, "Near–Infrared Spectroscopy of Synthetic Polymers," *Appl. Spec. Rev.* 1991, 26, pp. 227–339.

Martin, "Recent Advances in Near–Infrared Reflectance Spectroscopy," *Appl. Spec. Rev.* 1992, 27, pp. 325–383.

Geladi et al., "Linearization and Scatter–Correction for Near–Infrared Reflectance Spectra of Meat," *Appl. Spec.* 1985,, pp. 491–500, vol. 39, No. 3.

Isaksson et al., "The Effect of Multiplicative Scatter Correction (MSC) and Linearity Improvement in NIR Spectroscopy," *Appl. Spec.* 1988, , pp. 1273–1284, vol. 42, No. 7.

Aastveit et al., "Near–Infrared Reflectance Spectroscopy; Different Strategies for Local Calibrations in Analysis of Forage Quality," *Appl. Spec.* 1993, pp. 463–469 vol. 47, No. 4.

Isaksson et al., "Piece–Wise Multiplicative Scatter Correction Applied to Near–Infrared Diffuse Transmittance Data from Meat Products," *Appl. Spec.* 1993, pp. 702–709 vol. 47, No. 6.

Miller et al., "A Pathlength Correction Method for Near–Infrared Spectroscopy," *Appl. Spec.* 1990, pp. 895–898, vol. 44, No. 5.

Martens et al., *Multivariate Calibration*, John Wiley & Sons, New York, 1989, pp. 336–351.

Malinowski et al., *Factor Analysis in Chemistry*, John Wiley & Sons, New York, 1980, pp. 1–22 & 72–87.

Press et al., *Numerical Recipes: The Art of Scientific Computing*, 1986, Cambridge University Press, pp. 86–89.

*Primary Examiner*—Thomas P. Noland
*Attorney, Agent, or Firm*—Karen A. Harding; Harry J. Gwinnell

[57] ABSTRACT

In a process for analyzing a sample of unknown constitution by an analytical apparatus, a set of analytical measurements and a set of reference measurements, each comprising a set of multivariate signal responses obtained from a set of samples by a first and a second analytical apparatus, are adjusted to remove operational variabilities associated with the apparatus, thereby providing a first and a second matrix of adjusted signal responses. Via the use of matrix manipulations, a calibration useful for analyzing the signal responses obtained from the sample of unknown constitution by the first analytical apparatus is constructed and applied to the signal responses from the sample to determine its constitution.

18 Claims, No Drawings

PROCESS TO USE MULTIVARIATE SIGNAL RESPONSES TO ANALYZE A SAMPLE

FIELD OF THE INVENTION

This invention relates to analyzing a sample of unknown constitution, and more particularly to a process for analyzing a sample by constructing a calibration from multivariate signal responses perturbed by random multipliers.

BACKGROUND OF THE INVENTION

Calibration refers to the process of using empirical data and prior knowledge to determine how to estimate quantitative analyses from new measurements via some mathematical process.

Many analytical instruments provide responses that do not directly relate to desired quantitative measurements. For example, a chromatogram contains a series of peaks that relate to the amounts of components injected for analysis, but each component may have differing response factors that would bias the analysis unless a calibration were performed to determine and correct for these individual response factors.

Similarly, spectroscopic measurements such as those from infrared spectroscopy provide a vibrational spectrum that relates to the molecular motions of the individual components. Each vibrational motion has a certain response factor dependent on the characteristics of the molecule. For example, hydroxyl functionalities provide strong vibrational features, while carbon-sulfur bonds yield weak vibrational features in infrared spectra. The response factors affect the relative intensities of each vibrational band such that direct analysis of vibrational intensities will not yield accurate quantitative measurements. Calibration provides the means by which the relative response factors are accounted for in the transformation of the vibrational spectral data to quantitative measurements.

Near infrared spectrometry (NIRS) provides molecular vibrational motion data that is indirectly related to the desired quantitative measurement for many relatively complex chemical mixtures. NIRS instrumentation, data collection, and calibration are discussed in Stark et al., "Near-Infrared Analysis (NIRA): A Technology for Quantitative and Qualitative Analysis," *Appl. Spec. Rev.* 1986, Vol. 22, pp 335–399; Miller, "Near-Infrared Spectroscopy of Synthetic Polymers," *Appl. Spec. Rev.*, 1991, Vol. 26, pp 227–339; and Martin, "Recent Advances in Near-Infrared Reflectance Spectroscopy," *Appl. Spec. Rev.*, 1992, Vol. 27, pp 325–383, the disclosures of which are incorporated herein by reference. NIRS measures the absorbance of incident radiation at various wavelengths to ascertain a vibrational spectrum. The absorbance of radiation at different wavelengths indicates the presence of different vibrational motions, which in turn can be related to the desired quantitative measurements. NIRS is a highly useful technique that can provide quick and precise multivariate signal responses for on-line or in situ process environments.

Raman spectrometry is a complementary analytical technique to NIRS that also provides molecular vibrational information. Raman spectrometry measures the inelastic scattering of incident radiation from a sample and compares the inelastically scattered radiation to the incident radiation energy to provide an energy loss spectrum that relates to the vibrational motion of sampled molecules. The energy loss spectrum can be related to the desired quantitative measurements. Raman spectrometry can also provide a quick and precise multivariate signal response. Because of the contrasting nature of the scattering process in Raman compared to absorbance process in NIRS, different quantitative measurement problems can be solved by these two techniques.

There are often several interfering systematic or random effects that can disturb a representative multivariate signal response acquisition. Such effects rarely carry information that relates to the desired quantitative measurement. These effects may be caused by poor signal throughput, unstable radiation sources, unstable detector characteristics, random sporadic emissions, or various interfering background processes. It is common to reduce the impact of these effects on a subsequent calibration process by preprocessing the raw multivariate signal response. Useful preprocessing techniques include, for example: signal smoothing such as moving average filters and spline filters; double beam reference corrections such as the standardization method disclosed in U.S. Pat. No. 5,455,673; mean centering; differential derivative processing, i.e., computing a first or second derivative; spike filters; axis conversions, such as with spline functions; instrumental response compensations; and multiplicative signal correction estimation.

In their most useful applications, both NIRS and Raman spectrometry require the development of calibration models that correlate the acquired multivariate signal responses to quantitative measurements obtained by a reference technique. Correction and calibration of NIRS measurements is described in, for example, Geladi et al., "Linearization and Scatter-Correction for Near-Infrared Reflectance Spectra of Meat," *Appl. Spec.*, 1985, Vol. 39, pp 491–500; Isaksson et al., "The Effect of Multiplicative Scatter Correction (MSC) and Linearity Improvement in NIR Spectroscopy," *Appl. Spec.*, 1988, Vol. 42, pp. 1273–1284; Aastveit et al., "Near-Infrared Reflectance Spectroscopy: Different Strategies for Local Calibrations in Analysis of Forage Quality," *Appl. Spec.*, 1993, Vol. 47, pp. 463–469; Isaksson et al., "Piece-Wise Multiplicative Scatter Correction Applied to Near-Infrared Diffuse Transmittance Data from Meat Products," *Appl. Spec.*, 1993, Vol 47, pp 702–709; and Miller et al., "A Pathlength Correction Method for Near-Infrared Spectroscopy," *Appl. Spec.*, 1990, Vol 44, pp. 895–898, the disclosures of which are incorporated herein by reference.

All NIRS and Raman spectra of light diffusing solids are affected by particle size and by the presence of liquids in the sample. For example, in liquid samples the amount of turbidity, particulates, and bubbles, or changes in the solution refraction index may change the strength of the observed signal. For solid samples, the sample shape, uniformity, and thickness may change the strength of the observed signal. For powdered or granulated samples, the particle size, shape and/or the packing density of the material may change the observed signal strength.

When samples do not change with time, or if the spectra of time-dependent samples are collected in a multiplexed fashion, i.e., the responses at all wavelengths are measured simultaneously, the impact of changes in observed signal strength is to multiply each spectrum by an unknown constant that is unique to that individually collected spectrum. Spectral responses that have been multiplied by an unknown random number are not suitable for calibration directly using the usual multivariate statistical approaches such as PCR or PLS. Several approaches to dealing with normalization problems have previously been proposed, for example, in Martens and Naes, *Multivariate Calibration*, John Wiley & Sons, New York, 1989, pp. 336–351, the disclosure of which is incorporated herein by reference.

These approaches include normalization by closure, internal standards, and multiplicative scatter correction (MSC).

The normalization by closure method divides the original instrument responses at each point by the summation of all instrumental response points. This method is most useful when a relative instrumental response is adequate for the solution of the problem. However, in situations where the responses of the components vary greatly, the normalization by closure procedure can introduce artificial intercorrelations that makes it unsuitable for providing a spectral set in which the responses are proportional to the chemical compositions of the samples.

The use of an internal standard can be effective for solving some normalization problems. With this method, an additive having known response characteristics is introduced into the sample. The introduction of the additive provides a means to obtain a normalization constant by which the multivariate signal response can be corrected. While this method can be useful under some circumstances, it requires that an additive be introduced into the sample, which may not be practical in a production environment. Thus, the internal standard method does not provide a general solution to normalization problems.

The MSC method is based on the fact that the wavelength dependency of light scattering is different from that of chemically based light absorbance. Because of these dependencies, the data at many wavelengths can be used to distinguish, for example, between light absorption and light scattering. MSC may be suitable for analysis of an unknown sample containing several components, all of which have similar spectra, but it would not work well in situations where the spectral response represents several components varying over a wide composition range.

For the acquisition of quantitative measurements in production environments, one common approach to on-line monitoring is the continual removal from a stream of a small amount of material that is then processed through a "sampling system" to prepare it for the analysis. Commonly, the sampling system would condition the sample by, for example, removing bubbles, particulates, and turbidity; regulating temperature; or generally providing a constant observation condition. This would allow analytical apparatus such as a multivariate spectroscopy system to collect a spectrum that is reproducible to the extent necessary to relate to the constitution of the sample.

In favorable cases, the stream to be analyzed may have a spectral "signature" that enables the normalization of the spectral response. For example, one of the major components could have a distinct spectral response that does not interfere with the spectral response of other components in the sample. Under such limiting circumstances, variations in pathlength, turbidity or the like might be corrected by ratio methods to produce a robust calibration, but this approach would not be applicable to many industrial production situations.

It is also possible to estimate a calibration by using synthetic samples formulated in the laboratory to simulate what is thought to be in a process stream. However, practical experience indicates that it is usually better to calibrate the multivariate signal response in situ by measuring the multivariate signal response in the process and comparing it with quantitative measurements obtained from material samples removed from the manufacturing stream. In this situation, the spectra would contain all the variations of the real system of interest.

PROBLEM TO BE SOLVED BY THE INVENTION

Analysis of a sample of unknown constitution by an analytical apparatus often produces data that are perturbed by conditions prevailing at the data collection site. For example, if the sample under analysis were situated in a distillation column or reactor, the presence of bubbles or particulates could cause random variability in the sampling volume, preventing accurate analysis of the sample. Overcoming this effect of random variability requires construction of a calibration that compensates for sample volume discrepancies or other interferences that prevent a correct quantitative analysis. This need is met by the process of the present invention.

SUMMARY OF THE INVENTION

The present invention is directed to a process for analyzing a sample of unknown constitution by an analytical apparatus. The process utilizes a set of analytical measurements and a set of reference measurements obtained from a set of samples. The set of analytical measurements, which is obtained from the set of samples using a first analytical apparatus, comprises a first set of multivariate signal responses that is adjusted to remove operational variabilities associated with the first analytical apparatus, thereby providing a first matrix of adjusted signal responses. The set of reference measurements, which is obtained from the set of samples using a second analytical apparatus, comprises a second set of multivariate signal responses that is adjusted to remove operational variabilities associated with the second analytical apparatus, thereby providing a second matrix of adjusted signal responses.

One of the two matrices of adjusted signal responses is decomposed into a matrix product that comprises a matrix comprising a set of principal factors and a matrix comprising the amounts associated with each of the principal factors included in the set. A compressed signal response matrix product is constructed that comprises a matrix comprising a subset of the set of principal factors and a matrix comprising the amounts associated with each of the principal factors included in the subset. Using the latter matrix, a projection matrix is computed.

A first normalized matrix product comprising a normalization matrix and the other of the two matrices of adjusted signal responses is constructed. From the first normalized matrix product and the projection matrix a compressed normalized matrix product is constructed. Values of the normalization matrix that minimize the difference between the first normalized matrix product and the compressed normalized matrix product are computed, thereby producing an optimal normalization matrix.

A second normalized matrix product is constructed that comprises the optimal normalization matrix and the matrix of adjusted signal responses that had been decomposed into a matrix product comprising the matrices of the first set of principal factors and amounts associated with each of them. Using the other matrix of adjusted signal responses and the second normalized matrix product, a calibration useful for analyzing the signal responses obtained from the sample of unknown constitution by the first analytical apparatus is constructed. The calibration is applied to the signal responses from the sample, enabling its constitution to be accurately determined.

ADVANTAGEOUS EFFECT OF THE INVENTION

The process of the present invention, which includes a normalization step that compensates for variability in sample volumes or scattering efficiencies, or other interferences that may cause a multiplicative variation in the responses from different samples, is a significant improvement over traditional multivariate calibration methods. This process provides for accurate in situ calibration of a multivariate analysis of a sample of unknown constitution in the presence of turbidity, bubbles, and/or particulates, conditions that are encountered in many common industrial processes, such as distillation columns, precipitators, crystallizers, boiling liquids, and a variety of heterogeneous reactions.

DETAILED DESCRIPTION OF THE INVENTION

Many general approaches for the construction of calibration functions are known in the art. For example, multiple linear regression (MLR), principal component regression (PCR), and partial least squares regression (PLSR) entail statistically based processes that utilize multiple measurements of the multivariate signal responses to derive the "best" calibration model for the particular calibration approach employed. These approaches require that signal responses such as spectra be collected under substantially the same observation conditions. Thus, for example, transmission or transflectance NIRS spectra must be collected with the same path length in the sample, diffuse reflectance NIRS must be collected on samples with the same scattering efficiency, and Raman spectra must be collected with constant excitation intensity and a reproducible sample volume.

The simplest form of a calibration is often referred to as univariate regression, in which one variable is measured and one property is modeled. The solution of such a calibration problem can be described as determining the coefficients in equation (1).

$$y = b + m*x \qquad (1)$$

where y is the reference quantitative measurement of the analyte of interest, and m and b are constants that relate the instrumental response x to the constitution. This is easily solved by measuring x at various levels of y and fitting a straight line to the data. In this simplified case, if a random number multiplies x for each individual sample or observation, it is apparent that there is no way to solve for m and b without additional information. Further, univariate regression techniques are limited when more than one component has an influence at a given instrumental response.

In the more general case, several components respond at each wavelength, so the equation becomes:

$$y = b_0 + b_1*x_1 + b_2*x_2 + \ldots + b_n*x_n \qquad (2)$$

where the subscripts identify the constants and analytical responses for different wavelengths, delay times, shifts, or the like. This formulation of the problem allows the primary response(s) for one component to be corrected for interferences by other components through the use of additional analytical response information. In this case, enough samples with known composition must be measured to enable the solution of a set of equations for the $b_n$ constants.

When each multivariate signal response is multiplied by an unknown random number, equation (2) becomes:

$$y = b_0 + L*(b_1*X_1 + B_2*X_2 + \ldots + B_n*X_n) \qquad (3)$$

where L is a different constant for each sample, and thus, for each equation in a set of equations. This formulation of the problem provides a set of non-linear equations with no known general solution.

Another approach to the solution of equation (2) is multiple linear regression (MLR). MLR uses a series of matrix inversions to arrive at the unknown calibration constants. Because of mathematical complications in using matrix inversions, serious difficulties may be encountered in the application of MLR when components of the data are collinear, in which case solving for the calibration coefficients with MLR may be impossible.

Another general approach to constructing a calibration model makes use of data compression. Examples of data compression techniques include: principal factor analysis (PFA), principal component regression (PCR), and partial least squares regression (PLSR).

PFA, a least-squares technique that is sometimes referred to as principal component analysis (PCA), is described in Malinowski and Howery, *Factor Analysis in Chemistry*, John Wiley & Sons, New York, 1980, pp. 8–22, the disclosure of which is incorporated herein by reference. The use of this technique will be described subsequently.

In general, constructing a calibration requires one to obtain a set of independent, multivariate signal responses from a set of samples using a first analytical apparatus and a second set of responses from the set of samples using a second analytical apparatus, and finding the relationship between them. The process of the present invention utilizes a set of analytical measurements comprising a first set of multivariate signal responses obtained from a set of samples using the first analytical apparatus, together with a set of reference measurements comprising a second set of multivariate signal responses, which are obtained from the set of samples by a second analytical apparatus. The first set of multivariate signal responses, which may be perturbed by random multipliers, is adjusted to remove effects of operational variabilities associated with the first analytical apparatus, whereby a matrix X of adjusted signal responses is obtained. The second set of signal responses obtained from the set of samples by the second analytical apparatus is adjusted to remove operational variability effects associated with the second apparatus, thereby giving matrix Y.

Matrix X can be decomposed into matrix product AB, as follows:

$$X = AB \qquad (4)$$

where matrix B represents a set of principal factors and matrix A represents the amount of each of these principal factors. Each of the principal factors, also known as eigenvectors, that comprise matrix B is mathematically orthogonal to the remaining principal factors and represents a specific variance in the multivariate signal response. The first several principal factors comprise a subset that contains significant structural information, but successive factors contain diminishing amounts of information and more random variation, or noise. By selection of an appropriate subset of principal factors, structure variations can be enhanced and noise variations reduced.

As discussed in the previously mentioned reference of Malinowski and Howery, pp. 72–87, the disclosure of which is incorporated herein by reference, various criteria may be used to select the number of factors to be retained in the subsequent analysis. Ordinarily, a selection is made of some number of principal factors that contribute most to describing the variance in the X matrix. The matrix that represents a selected subset of principal factors is designated by a "hat" over the letter, e.g., $\hat{B}$.

Compression of the multivariate signal responses may be accomplished by selecting the principal factors that adequately describe the response with a minimum of noise. The selection of principal factors for the compressed subset can be achieved by observing the rate of change of variance as components are added, then constructing a subset of those factors that provide the most physically significant information. From this analysis, matrix $\hat{B}$, representing a principal factors subset, and matrix $\hat{A}$, representing the amounts associated with each of the principal factors subset, are constructed, the product of matrices $\hat{A}$ and $\hat{B}$ forming a compressed signal response matrix:

$$\hat{X} = \hat{A}\hat{B} \tag{5}$$

This approximation would allow the calibration problem to be redefined to overcome collinearity limitations and would be useful for the development of a calibration provided that each acquired spectrum had a consistent normalization multiplier. In many industrial process streams and/or with certain analytical instrumentation, however, it would be extremely difficult to meet this criterion. The process of this invention provides a unique solution to the calibration problem that does not require a consistent multiplicative multiplier, i.e., spectral path lengths or scattering volumes may vary.

Calibration processes proposed to date require that the whole set of spectra have reproducible intensities that are proportional to the constitution of the sampled material. In a number of potentially useful applications, both NIRS and Raman spectra are obtained that are of high quality except for the fact that the overall intensity varies from spectrum to spectrum. In the absence of a method to restore the proper spectral intensity, these intensity variations would frustrate efforts to achieve accurate calibration.

When the measurements obtained from one analytical apparatus for a sample are written as an ordered set of numbers, and the multivariate signal responses from a second analytical apparatus are written as an additional ordered set of numbers, these sets provide two distinct multivariate representations of the same sample. The calibration problem is one of finding a method that uses reference measurements on samples obtained with one apparatus to find both the normalization constants and the calibration coefficients that can be applied to information contained in the multivariate signal responses obtained from the samples using the other apparatus, thereby making both sets of analytical measurements equivalent. Prior to this invention, there has been no solution to this problem to provide calibration that enables useful analyses to be accomplished.

The first step of the process is to acquire a set of raw multivariate signal responses from a set of samples using the first analytical apparatus. These responses can be acquired with a variety of analytical apparatus, for example: Raman spectrometric, near-infrared spectrometric, ultraviolet spectrometric, nuclear magnetic resonance spectrometric, visible spectrometric, mass spectrometric, gas chromatographic, liquid chromatographic, gravimetric, volumetric, titrimetric, and viscometric apparatus. These instruments may comprise either the first or the second analytical apparatus in accordance with the invention. In preferred embodiments of the invention, the first apparatus is a Raman or a near-infrared spectrometer, and the second apparatus is a nuclear magnetic resonance spectrometer or a liquid or gas chromatographic apparatus. In these embodiments, the first set of analytical measurements comprises a Raman spectrum or a near-infrared spectrum, and the second set of reference quantitative measurements comprises a nuclear magnetic resonance spectrum or a liquid or gas chromatogram.

The absolute intensity of the signal responses is not critical; thus, for example, the path length of a Raman or NIRS measurement need not be held constant for different spectral acquisitions. The raw multivariate signal responses are then adjusted to remove the effects of operational variabilities associated with the analytical apparatus. Such adjustments may include, for example, adjusting baselines, taking derivatives, selecting a portion of the total response for use, and the like.

A PFA enables the total variance in the spectral set to be estimated and partitioned among the various principal components, thereby providing a basis for compressing matrix X. Matrix Y may be described in a similar fashion. In accordance with the process of the invention, the amounts A of each principal factor are constrained to be the same in both representations. Thus, the definition of Y becomes:

$$Y = AC \tag{6}$$

where the principal factors for Y are represented by C. Traditionally, the compression of Y has been done independently of X to retain quantitatively useful data contained in matrix Y while suppressing random noise. However, in the process of the present invention, the compression of Y is based entirely on information from matrix X.

By using A in the factor analysis of Y, an estimate of the principal factors that describe the measurements for each sample by a second analytical apparatus can be obtained. This procedure, which yields matrix $\hat{C}$ as the compressed subset of the principal factors of Y, deviates from the usual approaches to factor analysis in that it uses a PFA on one matrix as the basis for factoring a different, but presumably related, matrix.

Another important ingredient in the solution of the normalization problem is the determination of an appropriate way to include the normalization multipliers into the formulation of the process. If matrix Y is adjusted with a multiplicative diagonal normalization matrix N, then a normalized reference measurements matrix product W is obtained:

$$W = NY \tag{7}$$

W is in units proportional to the relative intensities in the rows of the X matrix and represents the normalized second matrix set for calibration. The inverse of the N matrix is the matrix needed to normalize the rows in the X matrix so that they have the correct intensity to match matrix Y.

A projection matrix $\hat{S}$ whose product with matrix W provides a compressed normalized reference measurements matrix $\hat{W}$ can be computed from $\hat{A}$, as follows:

$$\hat{S} = \hat{A}(\hat{A}^T\hat{A})^{-1}\hat{A}^T \tag{8}$$

In equation (8), $\hat{A}^T$ represents the transpose of $\hat{A}$, and $(\hat{A}^T\hat{A})^{-1}$ represents the inverse of $(\hat{A}^T\hat{A})$. The compression of W can then be represented as follows:

$$\hat{W} = \hat{S}W \tag{9}$$

Note that $\hat{W}$ includes information related to the principal components in X.

The difference between W and $\hat{W}$ is the cumulative result of errors in measurement of both the X and Y matrices, non-linearities in responses, and differences owing to the fact that the first and second sets of measurements are not proportional and have different normalization constants. Determining the set of normalization multipliers that minimize the differences between W and $\hat{W}$ produces an optimal set of normalization multipliers, which may be designated $N_O$.

The normalization constants found by this process are the inverse of those needed to normalize the multivariate signal responses, so the inverse of the optimum normalization matrix is used to adjust the multivariate signal responses to produce matrix $X_N$:

$$X_N = N_O^{-1} X \tag{10}$$

$X_N$ may be used with Y in any of the common multivariate analysis techniques, such as MLR, PCR, or PLSR, to construct a calibration useful for the quantitative determination of the constitution of an unknown sample by the first analytical apparatus. The calibration may be applied, for example, to a Raman or near infrared spectrum of the sample to correct the intensities of significant vibrational features and thereby allow an accurate quantitative analysis.

In accordance with the process of the invention, values of the normalization matrix N are determined that minimize the difference between W and $\hat{W}$. Several possible metrics can be chosen for this purpose, including: a sum of the absolute values of the individual errors, a sum of the squares of the errors, or various weighted sums of the errors. Any particular selection will lead to a particular estimate of the normalization constants. In a preferred approach, a sum of the squared errors is chosen as the error minimization metric. As noted above, the optimum value of the normalization matrix that minimizes the difference between W and $\hat{W}$ is designated $N_O$.

Optimization of the normalization multipliers can be accomplished by any of several methods, including iterative estimation or minimization procedures, or, preferably, by use of a set of derived equations. In one useful approach, a set of normalization constants is produced that provides a least root mean-square minimization of the difference between W and $\hat{W}$, which may be mathematically represented as minimizing expression (11) with respect to the $N_{k,k}$ for all k's.

$$\sum_{i=1}^{M} \sum_{j=1}^{n} \left( N_{i,i} Y_{i,j} - \sum_{q=1}^{M} \hat{S}_{i,q} N_{q,q} Y_{q,j} \right)^2 \tag{11}$$

In expression (11), M represents the number of samples in the set, and n represents the number of responses measured by the second analytical apparatus for each sample.

A preferred way of performing the minimization of expression (11) is to obtain the partial derivatives with respect to $N_{i,i}$ for all i's up to the number of spectra, and set the result equal to zero. The following equations result:

$$0 = \sum_{q=1}^{M} N_{q,q} \left\{ \sum_{i=1}^{n} Y_{q,i} Y_{k,i} \sum_{j=1}^{M} (\hat{S}_{j,q} - \delta_{j,q})(\hat{S}_{j,k} - \delta_{j,k}) \right\} \tag{12}$$

$$= \sum_{q=1}^{n} N_{q,q} D_{q,k}$$

where there is one equation for each sample. The term in equation (12) enclosed in braces defines the elements $D_{l,k}$. The symbol $\delta_{j,k}$ is the Kroeniker delta function, which has a value of one when j=k and zero otherwise. Because any arbitrary multiple of the X or Y matrices would also provide a solution to the equations, the degrees of freedom in these equations is one less than the number of samples. Thus, another equation is needed; a suitable choice is to have the sum of the coefficients equal the number of samples, M, or:

$$M = \sum_{q=1}^{M} N_{q,q} \tag{13}$$

Equations (12) and (13) may be combined by augmenting the D matrix with a row having each element equal to one and by defining a new matrix P which is a column matrix having zero in each element except for the last row, which has M in it. Then, the value of $N_O$ may be computed as:

$$N_O = (D^T D)^{-1} D^T P \tag{14}$$

In the particular operation represented by expression (11), each individual difference is identified and explicitly includes the normalization multipliers. This expression, which is derived by forming a sum of squares of those individual errors, enables an analytical minimization of the sum of squared errors that is represented by equation (12). When the condition provided in equation (13) is added to assure that the equations are soluble, a linear set of equations is found to describe the solution for the normalization constants. The approach represented by (11)–(14) provides a closed form solution using a set of linear equations for the normalization constants.

The described method is symmetrical in X and Y. The process of the invention has been described using matrix X of responses perturbed by random multipliers, with matrix Y representing reference measurements of the samples by a second analytical apparatus. However, the process of the invention can be applied equally beneficially in the situation where matrix Y represents the set of perturbed multivariate signal responses.

The process of the present invention provides accurate in situ calibration of multivariate analyses in the presence of turbidity, bubbles, and particulates, such as are frequently encountered in industrial processes, for example, distillations, polymerizations, heterogeneous reactions, precipitations, crystallizations, and the like. Thus, a sample of unknown constitution that is to be measured by an analytical apparatus can, for example, be situated within a distillation column or head. Alternatively, it may be a solid or a solid/liquid mixture. The sample may comprise the components of a reaction mixture such as, for example, a stream within a continuous reactor. The reaction mixture may comprise a plurality of phases—solid, liquid, and gaseous.

The following examples further illustrate the invention.

EXAMPLE 1

Calibration of Mixed Xylene Raman Spectra

The capability of the process of the invention was further demonstrated using a sample set of mixed xylenes. The samples were prepared by carefully weighing varying amounts of each component into the mixture. The molar concentration percentages of eleven samples containing p-, m-, and o-xylene, where the concentration of each component ranged from 25 to 40 mole percent, were calculated and used as the reference measurements (matrix Y).

A Raman instrument containing a 2.0 Watt multimode diode laser operating with 800 nm excitation and pigtailed to a 100-μm silica quartz core, fiber optic cable (Spectra Diode Lab, Inc., San Jose, Calif. model number SDL-2372-P3), was constructed. The incident radiation was split into two beams with a fiber optic beam splitter (Oz Optics Ltd., Carp, Ontario, Canada, model number FOBS-12-555-MMM-750-50/50), and both beams were focused onto individual 200-μm core, polyimide buffered, quartz silica fiber optic cable (Fiberguide Industries, Stirling, N.J.). The two fiber optics transmitted the radiation to both a sample probe and a reference probe.

The radiation in each fiber optic cable was filtered prior to entering the individual probes. The filters (Omega Optical, Brattleboro, VT model number 800 BP10) were designed to transmit only a narrow energy band and were inserted into a fixed fiber optic filter holding device (Oz Optics, Ltd. model number ND-200-55-750-M-30).

The reference fiber optic probe was used to illuminate a small diamond fragment, which was employed as the reference material. The sample probe was inserted into a 316 stainless steel sample tube in which the mixed xylene samples were placed.

The scattered radiation from both the reference and sample was collected by individual 200-µm fibers positioned closely about the excitation fibers. The collected scattered radiation was filtered to remove nearly all the Rayleigh scattered radiation prior to entering the return fiber. The filter (Omega Optical, model number 800 REFLP), which was held in a fixed fiber optic filter holding device (Oz Optics, Ltd. model number ND-200-55-750-M-30), was designed to pass the desired Raman scattered radiation while efficiently rejecting the unwanted radiation.

Both return fibers were directed back towards an Acton SpectraPro spectrograph (Acton Research Corporation, Acton, Mass.). The spectrometer was constructed with a turret-style grating system with three dispersive gratings. A 300 grooves/mm grating was used for the analysis and provided approximately 1700 $cm^{-1}$ spectral coverage.

A fiber adapter fashioned with eight 200-µm inputs was connected to the entrance of the spectrometer to enable up to eight Raman channel collection. The fibers were arranged into a linear array and positioned directly in front of the entrance slit. One of these eight spectrometer fibers was connected to the sample probe fiber and another was connected to the reference probe fiber. The dispersed radiation was detected by a Princeton Instruments (Trenton, N.J.) thermoelectric-cooled CCD detector and converted into an electronic signal. The CCD chip was a Techtronix 512 by 512 pixel, back-illuminated detection system.

The instrument was controlled with the CSMA data acquisition software provided by Princeton Instruments; 30-second spectra were acquired. A cubic spline interpolation as described in Press et al., *Numerical Recipes: The Art of Scientific Computing*, 1986, Cambridge University Press, pages 86–89, was used to provide equally spaced abscissa data. The standardization process described in U.S. Pat. No. 5,455,673 was applied to remove band shape and band position variations. The resultant standardized waveform was smoothed in the Fourier domain by a three point half width, Gaussian broadening and two point half width, Lorenztian narrowing function. The eleven standardized waveforms that correlated to the eleven reference measurements (matrix Y) were used as the multivariate signal responses (matrix X).

These values of X and Y were used to construct three calibration models. Calibration 1-1 utilized a 3 factor PLSR, and calibration 1-2 employed an MSC prior to construction of the PLSR. Calibration 1-3, in accordance with the process of the invention, combined a 3 factor normalization with a 3 factor PLSR to construct a calibration model.

An independent set of six validation mixtures having differing p-, m-, and o-xylene compositions were formulated from weighed amounts of the components. The molar percentage concentrations were calculated and compared with the quantitative analyses obtained from the corresponding standardized waveforms and each of the calibrations 1-1, 1-2, and 1-3. The RMS standard error for this validation set was determined for each chemical constituent and included in Table 1A.

TABLE 1A

| 26 Calibration Model | Calibration Method | RMS Standard Error of Validation | RMS Standard Error of Validation | RMS Standard Error of Validation |
|---|---|---|---|---|
| 1-1 Comparison | PLSR | 0.118 | 0.094 | 0.147 |
| 1-2 Comparison | MSC/ PLSR | 0.420 | 2.980 | 3.840 |
| 1-3 Invention | Normalization/ PLSR | 0.082 | 0.096 | 0.134 |

The data in Table 1A show an overall improvement by use of the process of the invention (calibration 1-3) over use of a 3 factor PLSR (calibration 1-1) and a substantial improvement over the MCS/PLSR method (calibration 1-2).

It should be kept in mind that the spectra in this example were obtained under well-controlled laboratory conditions. To simulate a bubbling/turbid stream of a production environment, each of the eleven standardized calibration waveforms and each of the six standardized validation waveforms were multiplied by randomly generated multiplicative constants ranging from 0.5 to 1.5.

Calibration 1-4 was constructed from the Y and X matrices data after the random multipliers had been applied. Calibration 1-5 was constructed from the perturbed matrices in accordance with the process of the invention. Table 1B contains the standard errors of validation determined after applying calibrations 1-4 and 1-5 to the six standardized validation waveforms and comparing them with the composition calculated for the formulated mixtures.

The results in Table 1B demonstrate the adverse effect of the applied random multipliers on the capability of calibration 1-4; compared with calibration 1-1, the standard error of validation was far worse for each constituent. In contrast, calibration 1-5, in accordance with the process of the invention, produced essentially the same results with the perturbed data sets as were obtained by calibration 1-3 for the unperturbed matrices.

TABLE 1B

| Calibration Model Number | Calibration Method | RMS Standard Error of Validation p-xylene | RMS Standard Error of Validation m-xylene | RMS Standard Error of Validation o-xylene |
|---|---|---|---|---|
| 1-4 Comparison | PLSR | 9.03 | 8.66 | 9.34 |
| 1-5 Invention | Normalization/ PLSR | 0.084 | 0.099 | 0.132 |

These results illustrate the capability of the process of the invention for constructing accurate calibration models. Since random effects, such as bubbling, turbidity, particulates, and the like that randomly alter sample volume are frequently encountered in production facilities, the present invention provides a valuable benefit in enabling the correct analysis of samples of unknown constitution under such adverse conditions.

EXAMPLE 2

On Line Polyester Manufacturing Calibration and Analysis

To demonstrate more fully the benefit of the process of the invention in a production situation, where fluctuations in process conditions cause disturbances in sampling volumes, a Raman instrument, constructed as described in Example 1, was placed in a polyester manufacturing facility. An optical probe was installed so that the sampling tip protruded into the flowing, molten polyester stream. A sample port was located within a few feet of the sample probe, and a small sample of the oligomer was removed every four hours. This sample was analyzed by nuclear magnetic resonance (NMR) to determine the extent of the first stage (transesterification) reaction.

The corresponding Raman spectra and NMR analytical results were arranged into matrix arrays and used to construct three distinct calibration models. The formulation of calibration 2-1 utilized a three factor PLSR, and calibration 2-2 made use of an MSC procedure prior to the PLSR. Calibration 2-3 was constructed in accordance with the process of the present invention. The standard errors of an independent validation set obtained by each of the calibrations are indicated in Table 2.

TABLE 2

| Calibration Number | Calibration Method | RMS Standard Error of Validation |
|---|---|---|
| 2-1 Comparison | PLSR | 9.07 |
| 2-2 Comparison | MSC/PLSR | 1.23 |
| 2-3 Invention | Normalization/ PLSR | 0.12 |

Examination of the collected Raman spectra revealed dramatic variations in the overall signal intensity. The effect of these disturbances is shown by calibration 2-1, where the disturbances in the Raman sample volume render the usual methods of calibration unreliable. An improvement was obtained by using the MSC/PLSR procedure of calibration 2-2. The small standard error obtained by the application of calibration 2-3 strikingly demonstrates the value of the present invention for the analysis of samples using multivariate signal responses obtained under production conditions.

The invention has been described in detail with particular reference to preferred embodiments thereof, but it will be understood that variations and modifications can be effected within the spirit and scope of the invention.

We claim:

1. A process for analyzing a sample of unknown constitution by an analytical apparatus utilizing a set of analytical measurements and a set of reference measurements obtained from a set of samples, said process comprising:

subjecting said set of samples to measurement using a first analytical apparatus, thereby obtaining a set of analytical measurements comprising a first set of multivariate signal responses;

adjusting said first set of multivariate signal responses to remove effects of operational variabilities associated with said first analytical apparatus, thereby obtaining a first matrix of adjusted signal responses;

subjecting said set of samples to measurement using a second analytical apparatus, thereby obtaining a set of reference measurements comprising a second set of multivariate signal responses;

adjusting said second set of multivariate signal responses to remove effects of operational variabilities associated with said second analytical apparatus, thereby obtaining a second matrix of adjusted signal responses;

decomposing one of said matrices of adjusted signal responses into a matrix product that comprises a matrix comprising a set of principal factors and a matrix comprising the amounts associated with each of said set of principal factors;

constructing a compressed signal response matrix product that comprises a matrix comprising a subset of said set of principal factors and a matrix comprising the amounts associated with each of the principal factors included in said subset;

computing a projection matrix from the matrix comprising the amounts associated with each of the principal factors included in said subset;

constructing a first normalized matrix product comprising a normalization matrix and the other of said matrices of adjusted signal responses;

constructing a compressed normalized matrix product comprising said projection matrix and said first normalized matrix product;

computing values of said normalization matrix that minimize the difference between said first normalized matrix product and said compressed normalized matrix product, thereby producing an optimal normalization matrix;

constructing a second normalized matrix product comprising said optimal normalization matrix and said one of said matrices of adjusted signal responses;

constructing from said other of said matrices of adjusted signal responses and said second normalized matrix product a calibration useful for analyzing the signal responses obtained from said sample of unknown constitution by said first analytical apparatus; and applying said calibration to analyze the signal responses obtained from said sample of unknown constitution by said first analytical apparatus, thereby enabling the constitution of said sample to be accurately determined.

2. A process according to claim 1, wherein the first set of multivariate signal responses adjusted to remove effects of operational variabilities associated with the first analytical apparatus comprises a first matrix X of adjusted signal responses, and the second set of multivariate signal responses adjusted to remove effects of operational variabilities associated with the second analytical apparatus comprises a second matrix Y of adjusted signal responses, said process further comprising:

decomposing matrix X into matrix product AB, wherein matrix B represents a first set of principal factors and matrix A represents the amounts associated with each of said first set of principal factors;

constructing a matrix $\hat{B}$ representing a principal factors subset and a matrix $\hat{A}$ representing the amounts associated with each of said principal factors subset, wherein the product of said matrices $\hat{A}$ and $\hat{B}$ forms a compressed signal response matrix $$\hat{X}=\hat{A}\hat{B};$$

computing from $\hat{A}$ a projection matrix $\hat{S}$, wherein $$\hat{S}=\hat{A}(\hat{A}^T\hat{A})^{-1}\hat{A}^T;$$

constructing from Y a first normalized matrix product W, wherein

W=NY,

N comprising a normalization matrix that renders W proportional to X;

constructing from $\hat{S}$ and W a compressed matrix product $\hat{W}$, wherein $\hat{W}=\hat{S}W$;

computing values of N that minimize the difference between W and $\hat{W}$, thereby producing optimal normalization matrix $N_O$;

constructing from $N_o$ and X a second normalized matrix product $X_N$, wherein $X_N = N_O^{-1}X$;

constructing from Y and $X_N$ a calibration useful for analyzing the signal responses obtained from said sample of unknown constitution by said first analytical apparatus; and applying said calibration to analyze the signal responses obtained from said sample of unknown constitution by said first analytical apparatus, thereby enabling the constitution of said sample to be accurately determined.

3. A process according to claim 1, wherein said first analytical apparatus is selected from the group consisting of a Raman spectrometric, a near-infrared spectrometric, an ultraviolet/visible spectrometric, a nuclear magnetic resonance spectrometric, a mass spectrometric, a gas chromatographic, a liquid chromatographic, a gravimetric, a volumetric, a titrimetric, and a viscometric apparatus.

4. A process according to claim 3, wherein said first analytical apparatus is a Raman spectrometric apparatus.

5. A process according to claim 4, wherein said set of analytical measurements comprises a Raman spectrum and said set of reference measurements comprises a nuclear magnetic resonance spectrum.

6. A process according to claim 3, wherein said first analytical apparatus is a near-infrared spectrometric apparatus.

7. A process according to claim 6, wherein said set of analytical measurements comprises a near-infrared spectrum and said set of reference measurements comprises a nuclear magnetic spectrum.

8. A process according to claim 1, wherein said second analytical apparatus is selected from the group consisting of a Raman spectrometric, a near-infrared spectrometric, an ultraviolet/visible spectrometric, a nuclear magnetic resonance spectrometric, a mass spectrometric, a gas chromatographic, a liquid chromatographic, a gravimetric, a volumetric, a titrimetric, and a viscometric apparatus.

9. A process according to claim 8, wherein said second analytical apparatus is selected from the group consisting of a nuclear magnetic resonance spectrometric, a gas chromatographic, and a liquid chromatograpic apparatus.

10. A process according to claim 9, wherein said set of reference measurements comprises a nuclear magnetic resonance spectrum and said set of analytical measurements comprises a spectrum selected from the group consisting of a Raman spectrum and a near-infrared spectrum.

11. A process according to claim 1, wherein said sample of unknown constitution comprises a liquid.

12. A process according to claim 11, wherein said liquid is near or at its boiling point.

13. A process according to claim 1, wherein said sample of unknown constitution comprises a solid.

14. A process according to claim 13, wherein said sample of unknown constitution further comprises a liquid.

15. A process according to claim 1, wherein said sample of unknown constitution comprises a liquid.

16. A process according to claim 15, wherein said sample of unknown constitution further comprises a vapor.

17. A process according to claim 1, wherein said sample of unknown constitution comprises the components of a reaction mixture.

18. A process according to claim 17, wherein said reaction mixture comprises a plurality of phases.

* * * * *